(12) United States Patent
Sommier et al.

(10) Patent No.: US 8,986,426 B2
(45) Date of Patent: Mar. 24, 2015

(54) METHOD FOR OPERATING AN ON-SITE MEDICAL GAS PRODUCTION PLANT AND ASSOCIATED PLANT

(71) Applicant: L'Air Liquide, Société Anonyme pour l'Etude et l'Exploitation des Procédés Georges Claude, Paris (FR)

(72) Inventors: Vincent Sommier, Paris (FR); Peter Neu, Duisburg (DE); Hartmut Franken, Krefeld (DE); Karsten Bongers, Krefeld (DE); Kais Maamar, Essen (DE)

(73) Assignee: L'Air Liquide, Société Anonyme pour l'Etude et l'Exploitation des Procédés Georges Claude, Paris (FR)

( * ) Notice: Subject to any disclaimer, the term of this patent is extended or adjusted under 35 U.S.C. 154(b) by 128 days.

(21) Appl. No.: 13/762,106

(22) Filed: Feb. 7, 2013

(65) Prior Publication Data

US 2013/0205997 A1 Aug. 15, 2013

(30) Foreign Application Priority Data

Feb. 14, 2012 (EP) ..................................... 12155273

(51) Int. Cl.
*F24F 3/00* (2006.01)
*B01D 53/053* (2006.01)
*B01D 53/02* (2006.01)
*B01D 53/30* (2006.01)
*A61M 16/10* (2006.01)

(52) U.S. Cl.
CPC ............... *B01D 53/02* (2013.01); *B01D 53/30* (2013.01); *B01D 53/053* (2013.01);
(Continued)

(58) Field of Classification Search
CPC .......... F24F 3/12; Y02C 10/08; B01D 53/02; B01D 53/30; B01D 53/053; B01D 2253/102; B01D 2253/104; B01D 2253/106; B01D 2253/108; B01D 2253/116; B01D 2256/12; B01D 2257/302; B01D 2257/404; B01D 2257/502; B01D 2257/504; B01D 2257/702; B01D 2257/80; B01D 2258/06; B01D 2259/401; B01D 2259/402; B01D 2259/403; B01D 2259/4533
USPC .......... 95/1, 8, 90, 96; 96/109, 111, 121, 397, 96/399; 128/204.18
See application file for complete search history.

(56) References Cited

U.S. PATENT DOCUMENTS 5,071,453 A * 12/1991 Hradek et al. ................... 96/111
5,199,423 A 4/1993 Harral et al.
(Continued)

FOREIGN PATENT DOCUMENTS

EP 0 297 542 1/1989
EP 0 537 612 4/1993
(Continued)

OTHER PUBLICATIONS

European Search Report and Written Opinion for EP 12 15 5273, Jun. 4, 2012.

*Primary Examiner* — Frank Lawrence
(74) *Attorney, Agent, or Firm* — Allen E. White (57) ABSTRACT

The invention relates to a method for operating a plant (100) for on-site production of medical gas, such as air or oxygen, comprising a main gas line (10) comprising, in series, a first vessel (A) for storing gas and a second vessel (B) for storing purified gas, and a secondary line (20) fluidically connected to the main line (10), downstream of the first vessel (A) for storing gas, and comprising a third vessel (C) for storing gas, the main gas line (10) and the secondary line (20) each supplying at least one gas consumer site (30), in particular a network of pipes in a hospital.

16 Claims, 2 Drawing Sheets

(52) U.S. Cl.
CPC .... *B01D 2253/102* (2013.01); *B01D 2253/104* (2013.01); *B01D 2253/106* (2013.01); *B01D 2253/108* (2013.01); *B01D 2253/116* (2013.01); *B01D 2256/12* (2013.01); *B01D 2257/302* (2013.01); *B01D 2257/404* (2013.01); *B01D 2257/502* (2013.01); *B01D 2257/504* (2013.01); *B01D 2257/702* (2013.01); *B01D 2257/80* (2013.01); *B01D 2258/06* (2013.01); *B01D 2259/40009* (2013.01); *B01D 2259/401* (2013.01); *B01D 2259/402* (2013.01); *B01D 2259/403* (2013.01); *B01D 2259/4533* (2013.01); *Y02C 10/08* (2013.01); *A61M 16/101* (2014.02)
USPC ............... 95/8; 96/111; 96/399; 128/204.18

(56) References Cited

U.S. PATENT DOCUMENTS

| | | | |
|---|---|---|---|
| 5,809,999 | A | 9/1998 | Lang |
| 5,915,834 | A | 6/1999 | McCulloh |
| 6,125,655 | A | 10/2000 | Millet et al. |
| 6,270,557 | B1 | 8/2001 | Millet et al. |
| 6,394,089 | B1 * | 5/2002 | Cantrill et al. ............ 128/205.12 |
| 6,478,857 | B2 * | 11/2002 | Czabala ........................ 96/130 |
| 7,204,249 | B1 * | 4/2007 | Richey et al. ............ 128/204.18 |
| 2004/0079359 | A1 | 4/2004 | Aylsworth et al. |
| 2004/0103895 | A1 | 6/2004 | Richey et al. |
| 2007/0214960 | A1 | 9/2007 | Aylsworth et al. |

FOREIGN PATENT DOCUMENTS

| | | |
|---|---|---|
| EP | 0 716 274 | 6/1996 |
| EP | 0 718 024 | 6/1996 |
| EP | 0 864 818 | 9/1998 |
| EP | 0 922 482 | 6/1999 |
| EP | 0 930 089 | 7/1999 |
| EP | 1 004 341 | 5/2000 |
| EP | 1 393 794 | 3/2004 |
| FR | 2 658 155 | 8/1991 |
| GB | 1 551 348 | 8/1979 |

\* cited by examiner

METHOD FOR OPERATING AN ON-SITE MEDICAL GAS PRODUCTION PLANT AND ASSOCIATED PLANT

CROSS REFERENCE TO RELATED APPLICATIONS

This application claims the benefit of priority under 35 U.S.C. §119 (a) and (b) to European Application No. 12155273.1 filed Feb. 14, 2012, the entire contents of which are incorporated herein by reference.

BACKGROUND

The invention relates to a plant for medical air production on-site, that is to say in a hospital building or the like, and to a method for controlling or operating such a plant.

The medical air used in hospitals, clinics, treatment centers, emergency or incident units, or the like, for patients' respiration is a medicament whose composition is specified by the European Pharmacopoeia.

More precisely, medical air is ambient air compressed to a pressure above atmospheric pressure, typically several bars, or to tens or even hundreds of bars and containing (by volume) from 20.4% to 21.4% oxygen, at most 500 ppm $CO_2$, at most 5 ppm CO, at most 1 ppm $SO_2$, at most 2 ppm NO and $NO_2$, at most 67 ppm water and at most 0.1 mg/m$^3$ oil; the oil vapors possibly present come essentially from the compression of the air.

It should be noted that, other than oxygen, the components mentioned above (i.e. COx, NOx, water, or oil etc.) are in fact impurities whose presence is tolerated within the limits of the Pharmacopoeia but which ideally are not present therein.

Medical air furthermore contains nitrogen, and may also contain other compounds, such as argon.

Currently, medical air is delivered to hospitals or the like in three forms, namely, depending on the case:
  direct delivery in the form of compressed air, for example at an absolute pressure of from 200 to 300 bar, in cylinders, that is to say bottles or canisters of gas, or containers comprising a plurality of bottles;
  production on-site by mixing oxygen and nitrogen so as to create nitrogen/oxygen mixtures, and
  direct production on-site from ambient air treated, in particular, by compressors and filtration/purification systems.

Of these, the production of air directly on-site by compressors and filtration systems is the most widespread solution. Such a method is described, for example, in the document EP-A-864818.

The ambient air is taken in and compressed by compressors to a pressure range extending from 1 bar to 80 bar relative. This compressed air is then filtered, that is to say purified, by means of one or more treatment steps, for example a set of filters and/or by employing a pressure swing adsorption method (PSA).

The medical air produced in this way may be stored in one or more intermediate buffer vessels, then sent through the network of pipes which passes through the hospital building in order to provision the treatment rooms, bedrooms or the like with medical air. It is quite clearly possible, and even indispensable in certain cases, to carry out intermediate expansion of the gas, for example in order to change from a pressure of about 10 bar in the storage vessel to a pressure of 5 or 8 bar in the network.

In general, any break in medical air provision is overcome by using medical air taken from a reserve or backup source in which the air is kept in gaseous form.

The other medical gases used in hospitals or treatment centers, such as oxygen, are also delivered in a similar way to the air. The compositions of these other gases are also specified by the European Pharmacopoeia.

Thus, oxygen may also be produced on-site by a PSA method by using specific adsorbents, such as lithium-exchanged zeolites X, making it possible to retain the nitrogen contained in the air and thus produce gaseous oxygen having a purity typically greater than 90%, or even 93% by volume, as is known from the document EP-A-297542.

However, the methods for producing medical air or other medical gases have used on-site (also referred to as on-site methods) present certain drawbacks.

First, these methods do not permit easy monitoring of the reliability of the manufacturing process.

Thus, when an on-site medical air production unit is operating autonomously, the manufacturing process is not overseen continuously and the interventions on the plant take place on the basis of planning, that is to say preventive maintenance, or when an error or a problem arises in the plant, that is to say curative maintenance.

These interventions are therefore carried out independently of the status of the plant and its reliability, which is not optimal because they are carried out either too soon, and therefore without actual need, or too late, and therefore with an impact on the production process and possibly on the final product.

Next, pollutant blockages in the main pipe occur when the gas produced is not compliant. This is because in existing plants, the control solenoid valve is a so called "2-way" solenoid valve which is arranged on the main line.

Although it makes it possible to stop possible pollution upstream of the valve, this pollution nevertheless remains blocked in the main line and necessitates a total purge of the system upstream of the valve. This is not ideal because it entails a shutdown of the gas production and manual intervention.

Furthermore, in the event of short-term breaks in the air provision due, for example, to temporary contamination at the inlet, the backup source is resorted to directly. However, this poses a problem because the backup volume is limited and therefore, if the frequency of the breaks in provision is high, there is then a risk of draining the backup source. In other words, it would be highly beneficial to be able to avoid this drawback by reducing the extent to which the backup source is used, so as to increase its autonomy over time.

Lastly, the air produced by the current methods and plants is in general neither analyzed nor validated in pharmaceutical terms, which may raise obvious problems of compliance and quality. Furthermore, when it is analyzed, in the event of "noncompliance" this usually leads either to immediate interruption of the production and changeover to a backup air source, and which may entail overuse of the backup air liable to cause a possible total break in the air provision, or to continuous provision of noncompliant air and parallel triggering of an alarm in order to warn the user, who then needs to intervene manually. It will be understood that these solutions are not ideal either.

In summary, there is currently no method of validating air produced on-site which makes it possible to ensure that the air produced is in fact compliant with the required specifications and which makes it possible to ensure effective and reliable provision of medical air.

In other words, the problem which arises is to provide a plant for continuous on-site production of a medicament gas, particular medical air, in accordance with good manufacturing practice (GMP) and a method for controlling or operating such a plant, which permit in particular:

- supervision of the reliability of the manufacturing process with rapid detection of any anomaly,
- monitoring of the various production steps and in particular the final production with, for each step, the possibility of a purge thus making it possible to stop any contamination or noncompliance of the gas produced, in particular medical air, and/or
- the use of the backup sources to be reduced to a minimal level.

SUMMARY

The solution of the invention is a plant for on-site production of medical gas, in particular medical air, comprising:
- a gas purification unit adapted to produce a purified gas from a supply gas,
- a main gas line supplied with gas by the gas purification unit and comprising, in series, a first vessel for storing gas and a second vessel for storing purified gas, and
- a secondary line fluidically connected to the main line, downstream of the first vessel for storing gas and comprising a third vessel for storing gas,
- at least one gas analysis device arranged so as to determine the level of at least one given impurity in the gas, downstream of the second and third vessels,
- a first solenoid valve, arranged on the main gas line between the first vessel for storing gas and a second vessel for storing gas,
- a second solenoid valve, arranged on the secondary gas line between the first vessel and the third vessel for storing gas,
- a third solenoid valve, arranged on the main gas line downstream of the second vessel for storing gas,
- a fourth solenoid valve, arranged on the secondary gas line downstream of the third vessel for storing gas, and
- an operating device which controls the opening and/or closing of the said solenoid valves in response to at least one impurity level measurement signal received from the said at least one gas analysis device.

Depending on the case, the plant of the invention may comprise one or more of the following technical characteristics:
- a three-way solenoid valve is arranged on the main gas line between the gas purification unit and the first storage vessel.
- the three-way solenoid valve is connected to the atmosphere via a vent line, and is controlled by the operating device. Preferably, the gas present in the main pipe, upstream of the three-way solenoid valve, is diverted to the vent line and the delivery of gas to the first storage vessel is simultaneously stopped, when the impurity level measured in the main pipe is greater than or equal to a preset threshold level. Gaseous flushing of the pipe part contaminated with impurities is then carried out with purified gas and the gas flow thus generated is discharged to the atmosphere via the vent line.
- the main line and the secondary line supply one or more gas consumer sites, preferably a network of pipes.
- it includes a first gas analysis device having a first measurement line fluidically connected to the main line, upstream of the first storage vessel.
- the operating device controls the three-way solenoid valve in response to the measurements taken by the first gas analysis device.
- it includes a second gas analysis device having at least one second measurement line fluidically connected directly or indirectly to the main line and/or to the secondary line, downstream of the second storage vessel and/or downstream of the third storage vessel, respectively.
- it includes a first purge line fluidically connected to the main line downstream of the second vessel.
- it includes a second purge line fluidically connected to the secondary line downstream of the third vessel.
- the second gas analysis device is fluidically connected to the main line and to the secondary line, preferably downstream of the second and third vessels.
- the first purge line and/or the second purge line are fluidically connected to the vent line.
- the first purge line comprises a fifth solenoid valve and/or the second purge line comprises a sixth solenoid valve.
- the second measurement line comprises a seventh and/or an eighth solenoid valve.
- the said fifth, sixth, seventh and/or eighth solenoid valves are controlled by the operating device.
- a gas compression unit supplies the gas purification unit with a gas to be purified, such as air, compressed to a pressure higher than 1 bar absolute.
- the gas compression unit comprises at least one screw, piston, scroll or diaphragm compressor.
- the gas purification unit comprises at least one adsorber containing at least one bed of at least one adsorbent material.
- the gas purification unit comprises at least two adsorbers operating alternately, preferably according to PSA cycles.
- the operating device furthermore controls the gas purification unit and/or the gas compression unit.
- the operating device cooperates with the first and/or second gas analysis device.
- the gas to be purified is ambient air.
- the purified gas is medical air or medical oxygen, that is to say a gas compliant with the specifications of the European Pharmacopoeia.

The invention also relates to a method for operating an on-site medical gas, in particular medical air, production plant comprising a main gas line comprising, in series, a first vessel for storing gas and a second vessel for storing purified gas, and a secondary line fluidically connected to the main line, downstream of the first vessel for storing gas, and comprising a third vessel for storing gas, the main gas line and the secondary line each supplying at least one gas consumer site, in particular a plant according to the invention as described above, comprising the steps of:

a) supplying the said at least one consumer site with purified gas having a desired composition coming from the third vessel,
b) supplying the second vessel with gas coming from the first vessel for storing gas,
c) stopping the supply of the second vessel with the gas coming from the first vessel for storing gas when the second vessel is filled with gas,
d) analyzing the composition of the gas stored in the second vessel in order to determine whether the composition of the gas stored in the second vessel is compliant with the desired composition,
e) as a function of the result of step d), sending the gas stored in the second vessel:

i) either to the atmosphere when the analyzed composition is not compliant with the desired composition, ii) or to the said at least one consumer site when the analyzed composition is compliant with the desired composition.

Depending on the case, the method of the invention may comprise one or more of the following technical characteristics:

- in step e) ii), the said at least one consumer site starts to be supplied with gas stored in the second vessel after a shutdown of the supply of the said consumer site with gas taken from the third vessel.
- steps a) and b) are at least in part simultaneous.
- in step e) i), the second vessel is emptied fully or substantially fully and steps b) to e) are repeated.
- the second and third vessels operate so as to undergo steps a) to e) alternately.
- the gas supplying the second and third vessels is produced by a gas purification unit comprising at least one adsorber containing at least one bed of at least one adsorbent material, preferably at least two adsorbers operating alternately, the said at least one adsorber being supplied by a gas compression unit with gas to be purified.
- in step d), the composition of the gas is analyzed by means of at least one gas analysis device arranged so as to determine the level of at least one given impurity in the gas, downstream of the second and third vessels, the impurity or impurities preferably being selected from NOx, SOx, COx, water vapor and hydrocarbon vapors, in particular oil vapors.
- steps a) to e) are controlled by an operating device acting on valves arranged on the main gas line, the secondary line, on the first purge line fluidically connected to the main line downstream of the second vessel, and/or the second purge line fluidically connected to the secondary line downstream of the third vessel, as well as on the analysis line/lines.
- the gas produced is medical air or medical oxygen, preferably medical air.
- the medical air produced contains (by volume) from 20.4% to 21.4% oxygen, at most 500 ppm $CO_2$, at most 5 ppm CO, at most 1 ppm $SO_2$, at most 2 ppm NO and $NO_2$, at most 67 ppm water, at most 0.1 mg/m$^3$ oil, and nitrogen.

BRIEF DESCRIPTION OF THE DRAWING

The present invention will now be described in more detail with reference to the appended figures, in which.

DESCRIPTION OF PREFERRED EMBODIMENTS

Figure 1:
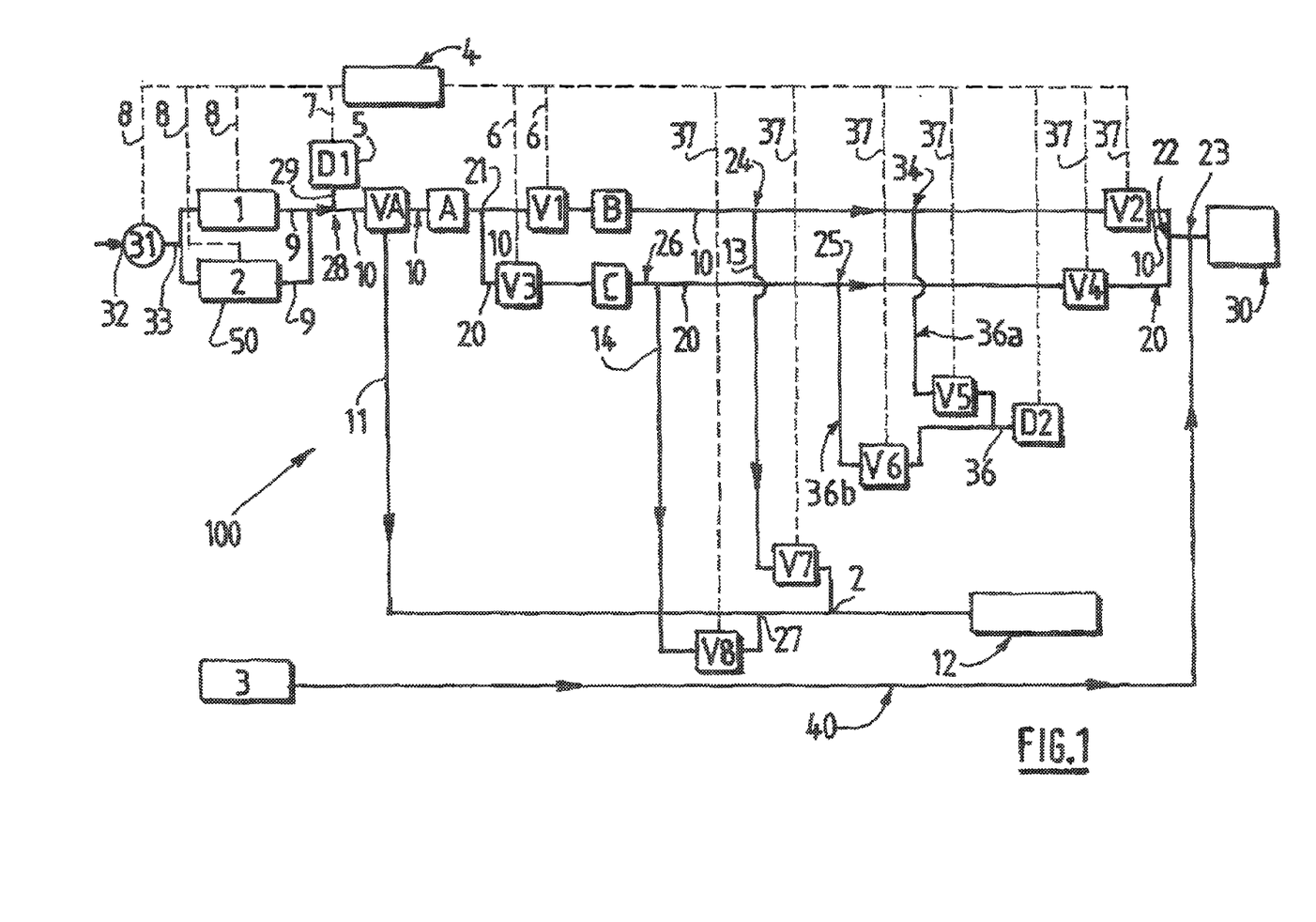
FIG. 1 represents a block diagram of a plant 100 for on-site production of medical gases according to the invention.

FIG. 1 is a block diagram of an embodiment of a plant 100 for on-site production of medical gases, which is controlled by the operating method according to the invention and is connected to the network of pipes 30 of a hospital building or the like.

The gas produced here is medical air, that is to say purified air satisfying the specifications of the European Pharmacopoeia mentioned above. Nevertheless, such a plant 100 may be used for manufacturing other medical gases, for example medical oxygen from ambient air.

More precisely, according to this embodiment, the on-site medical air production plant 100 comprises a gas purification unit 50 supplied by a gas compression unit 31, that is to say one or more air compressors taking in ambient air (at atmospheric pressure: 1 atm) through their supply inlet 32 and delivering compressed air at a pressure higher than atmospheric pressure, for example at a pressure of between 1 bar and 80 bar absolute. This compressor or these compressors 31 may be one or more screw, piston, scroll or diaphragm compressors.

The compressed air supplies the gas purification unit 50, which here comprises two adsorbers 1, 2 operating in parallel according to cycles of the PSA type (Pressure Swing Adsorption), that is to say one is in production phase while the other is in regeneration phase, and vice versa. Typically, the duration of a production cycle is between 1 and 30 minutes, approximately, preferably from less than 10 to 15 minutes.

These adsorbers 1, 2 each contain at least one bed of at least one adsorbent material, for example adsorbents such as zeolites, aluminas, active carbon, silica gel or any other molecular sieve capable of stopping the impurities present in ambient air.

In order to improve the purification of air and the elimination of the impurities, the presence of filters may also be provided, for example an active carbon filter and/or other filters capable of stopping all or some of the impurities to be eliminated.

Depending on the embodiment in question, the gas purification unit 50 may also comprise a single adsorber or more than 2 adsorbers 1, 2, for example at least 3 adsorbers.

These types of adsorbers 1, 2 and PSA cycle are well known and, in this regard, reference may furthermore be made for example to the documents EP-A-716274, EP-A-718024, EP-A-922482, GB-A-1551348, EP-A-930089.

In all cases, the adsorbers 1, 2 make it possible to eliminate all or some of the impurities which are possibly present in the ambient air to be purified or which have been introduced therein during the compression at 31, in particular water vapor, oil vapors, SOx, COx and/or NOx, so as to produce air of medical quality or medical air compliant with the European Pharmacopoeia.

Next, the purified air (or any other medical gas) produced by the gas purification unit 50 is recovered in outlet conduits 9 which supply a main line conveying gas, that is to say a pipe or a tube delivering gas, which is adapted and designed to convey the purified air produced in this way to a first storage vessel A, that is to say a buffer vessel, in which the purified medical air can be stored and homogenized before being sent to one or more consumer sites 30, such as a network of gas pipes passing through a hospital building in order to convey the medical air to the various rooms in which it is to be used, such as treatment rooms, emergency rooms, recovery rooms, bedrooms or any other any other location.

The main gas line 10 therefore fluidically connects the outlet (or outlets) 9 of the gas purification unit 50 to the said first storage vessel A so as to supply it with purified air coming from the two adsorbers 1, 2 of the gas purification unit 50.

The operation of the compressor or the compressors 31 and the purification cycles taking place in the gas purification unit 50 are controlled and monitored by an operating device 4, for example a programmable automaton or the like, connected to the gas purification unit 50 by electrical connections 8, such as electrical cables.

It should, however, be noted that the communication between the various elements and devices of the plant, in particular with the automaton 4, could in general also take place via wireless links, for example via one or more wireless transmitter devices or systems such as radiofrequency (RF), Bluetooth, Zigbee, wifi, GSM or GPRS, and one or more receiver antennas for carrying out wireless transmissions of data adapted to the type of transmitter used.

Preferably, the automaton 4 or the like is programmed according to the requirements of the hospital site in question and can be reprogrammed if the requirements of the site change, for example.

In order to regulate and monitor the conveyance of gas in the main gas line 10, a solenoid valve VA is arranged on the said main line 10 between the gas purification unit 50 and the first storage vessel A. The solenoid valve VA is also controlled by the operating device 4 via an electrical connection 5, such as an electrical cable.

The valve VA is a three-way solenoid valve, one of the ports of which is fluidically connected via a vent line 11 to the ambient atmosphere (at 12) where there is preferably a device for venting to the atmosphere, such as a vent valve (not represented), and the other two ports of which are fluidically connected to the main line 10.

The air produced by the gas purification unit 50 therefore passes through two of the three ports of the solenoid valve VA, that is to say the first and second ports of the solenoid valve VA, when it passes normally through the said solenoid valve VA in the direction of the buffer vessel A where the purified gas can be stored.

Conversely, in the event of contamination of the line 10 upstream of the valve VA, this pollution can be expelled easily and effectively from the contaminated conduit portion of the main line 10, without the need for a total purge of the system upstream of the valve VA.

This is done conventionally by flushing the conduit portion polluted by the impurities with pure air produced by the gas purification unit 50. The gas flow entraining the impurities is then discharged via the third port of the solenoid valve VA to the atmosphere, through the vent line 11 to the ambient atmosphere. In other words, the air produced by the gas purification unit 1, 2 will then entrain the pollutants with it and these will be disposed of to the atmosphere (at 12).

The 3-way solenoid valve VA therefore makes it possible not only to block any possible pollution on the main line 10 in order to confine it upstream of the solenoid valve VA, but also subsequently to discharge this pollution of the main line 10 to the outside (at 12) and thus to purge the main line 10 upstream of the valve VA.

This makes it possible to avoid shutting down the production process entirely and resorting to the backup 3, that is to say a pure gas reserve, in the event of temporary pollution of the air taken in or created by the production line.

Furthermore, the first buffer vessel A makes it possible to take over the delivery of the purified gas, such as medical air, when the valve VA is in the vent position, that is to say when a purge of the line 10 is ongoing, so as here again to reduce the frequency of use of the backup source 3.

The first vessel A also makes it possible to protect the production unit 50 from consumption peaks, that is to say peaks in demand from the consumer sites 30, and to homogenize the air produced by the production unit 50.

The monitoring of the composition of the gas produced, such as purified air, delivered by the production unit 50 is carried out by means of a first gas analysis device D1, such as an analysis cabinet or any other suitable gas analyzer, the measurement line 29 of which is connected fluidically (at 28) to the main line 10, upstream of the 3-way valve VA.

This gas analysis device D1 is connected to the operating device 4 via an electrical connection 7, such as an electrical cable or the like, so as to transmit measurement signals and optionally other information thereto. As a function of the signals received, the operating device 4 can retroact on the 3-way valve VA and preferably the other elements of the plant, such as production unit 50, compressor 31, etc., in order to trigger a purge of the line 10 when pollution is detected.

More precisely, in order to evaluate the reliability of the method and of the production plant, the quality of the air produced is analyzed using the analysis cabinet D1, in particular the levels of $H_2O$, $CO_2$ and oil vapor, so as to ensure that the air produced is compliant with a desired composition, in particular that of the European Pharmacopoeia mentioned above.

Complementary monitoring variables (for example temperature, pressure, vibrations, etc.) are furthermore collected from the plant. The analysis results as well as the monitoring variables are then processed by the operating device 4, such as an automaton, on the basis of statistical process control (SPC) in order to define the reliability of the production process.

The processing of the data is carried out for each of the production lines, that is to say for each of the adsorbers 1, 2 of the production unit 50 as well as the compressor is 31, on the basis of conventional control elements, such as aptitude indicators of the production process, control chart of the variables, average, control limits trend analysis of the variables, etc.

On the basis of the results and the predefined parameters, it is then possible to determine whether or not the manufacturing process is reliable.

If the manufacturing process is no longer reliable, the production line in question, that is to say the adsorbers 1 or 2 and the associated compressor 31, is shut down and the second line, that is to say the other adsorber 2 or 1, respectively, takes over for producing purified air, while the other line is regenerated, reinitialized and/or undergoes a maintenance operation.

In the event of unreliability of the second line, the system then switches to the backup source 3. Specifically, the plant also comprises a backup line 40 fluidically connecting a backup source 3, such as a backup reservoir containing medical air, to the gas consumer sites 30, directly or indirectly, that is to say by being connected at 23 to the main gas line 10 or to a secondary line 20.

The secondary line 20 is in fact another gas line arranged in parallel with the main line 10 and used as an alternative passage for the gas coming from the vessel A, for example, and/or from the production unit 50.

During normal operation, the gas sent to the consumer sites 30, such as a network of gas conduits in a hospital building, is in fact provided alternately by the gas storage vessels B and C according to the cyclic process described below.

These vessels B, C are in fact used to supply the consumer site or sites 30 alternately with respiratory gas, i.e. to provide medical air in alternation, that is to say while one vessel (for example B) is being filled or analyzed for compliance, the second (respectively C) delivers the gas to the hospital network 30, or vice versa.

In other words, the main gas line 10 branches (at 21) downstream of the first vessel A into the secondary line 20. The latter 20 is therefore fluidically connected on its upstream side (at 21) to the said main line 10 and, by its downstream end, to at least one gas consumer site (30), directly or indirectly, that is to say by being connected (at 22) to the main gas line 10.

The line 10 comprises a second buffer vessel B for storing purified gas, located between the first vessel A and the gas consumer site or sites, such as a network of pipes 30 of a hospital building, and the secondary line 20 in turn comprises a third vessel C for storing purified gas.

Figure 2:
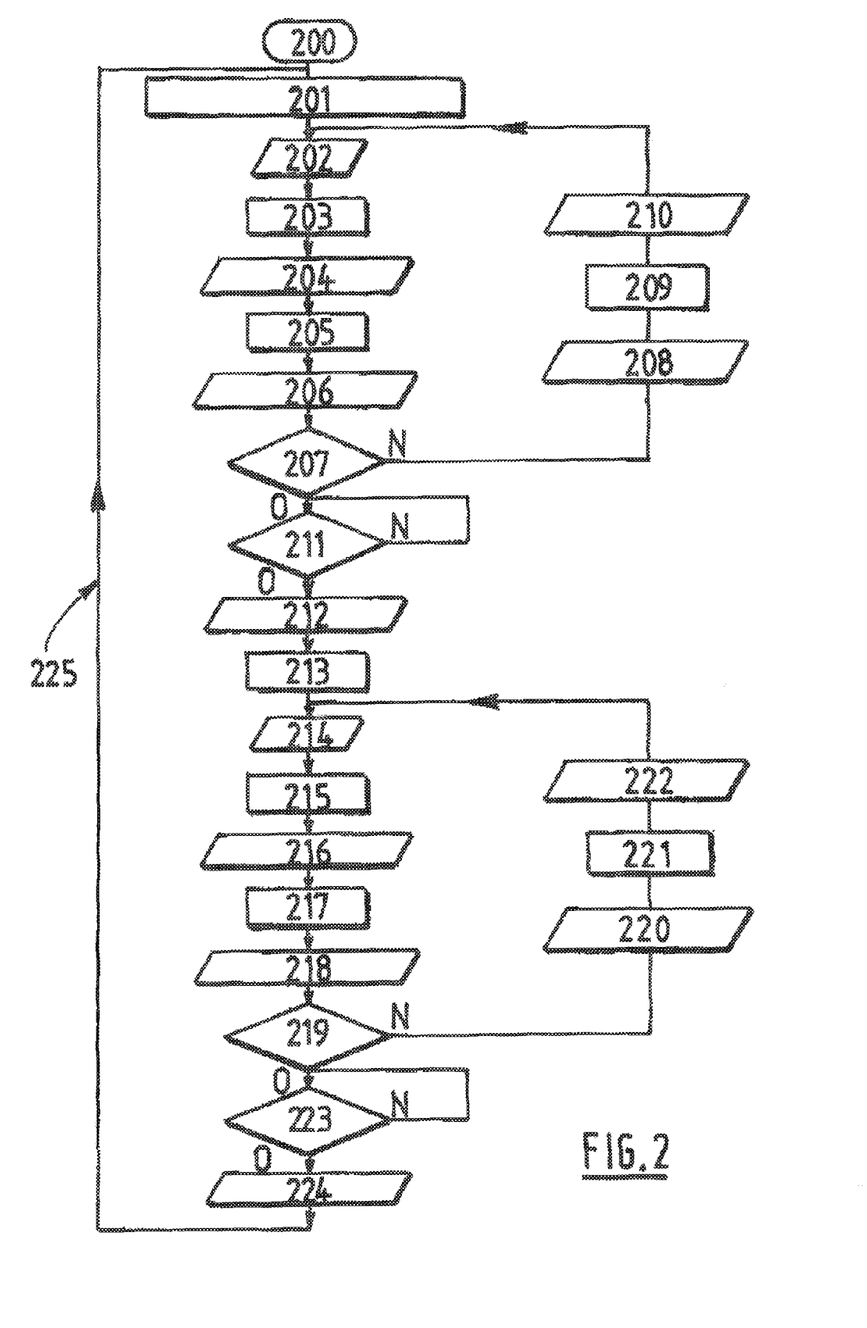
FIG. 2 illustrates the various steps of the method according to the present invention for controlling the plant of FIG. 1.

As already mentioned, the storage vessels B, C are used to supply the consumer site or sites 30 according to a well-determined sequence or process cycle, which is illustrated in FIG. 2, while ensuring that the air sent to the consumer sites 30 is indeed compliant with the specifications of the Pharmacopoeia, that is to say that it is in fact air of medical quality (medical air) and, in the converse case, to take the measures necessary in order to evacuate any noncompliant air to the atmosphere, as described in detail below.

In general, maintenance of the plant 100 is triggered by the automaton 4 on an anticipatory basis when the production parameters of one or both production units 1, 2 reach a predetermined threshold.

It will furthermore be noted that 2-way solenoid valves are arranged on the main line 10 and the secondary line 20. More precisely, a first solenoid valve V1 is arranged between the first vessel A and the second vessel B, and a second solenoid valve V3 is arranged between the first vessel A and the third vessel C for storing purified gas. Furthermore, a third solenoid valve V2 is arranged downstream of the second vessel B and a fourth solenoid valve V4 is arranged downstream of the third vessel C. These 2-way solenoid valves are controlled by the operating device 4 via electrical connections 6, 37, such as cables or the like, and make it possible to control the passage of the gas through the lines 10 and 20 and therefore to divide the pipes 10, 20 into well-determined sections, and also to manage and/or operate the gas inlets and/or outlets of the vessels B and C.

The plant 100 furthermore comprises a first purge line 13 fluidically connected by its upstream end 24 to the main line 10, preferably downstream of the second vessel B, and by its downstream end 25 to the vent line 11, as well as a second purge line 14 fluidically connected by its upstream end 26 to the secondary line 20, preferably downstream of the third vessel C, and by its downstream end 27 to the vent line 11.

The first purge line 13 comprises a fifth solenoid valve V7 and the second purge line 14 comprises a sixth solenoid valve V8 used to control the passage of the gas to the vent line 11. The operating device 4 also controls the solenoid valves V7, V8 via the electrical connections 37.

These purge lines 13, 14 make it possible to purge the portions of lines 10, 20 as well as the vessels B and C, respectively, located upstream of the solenoid valves V2 and V4, respectively.

A second gas analysis device D2, such as an analysis cabinet or the like, is provided and includes at least one second measurement line 36, branching into two subsections 36a, 36b, which is fluidically connected (at 34, 35) to the main line 10 and to the secondary line 20, in particular by means of the subsections 36a, 36b. Preferably, the second measurement line 36, 36a, 36b comprises a seventh V5 and/or an eighth V6 solenoid valve.

This second gas analysis device D2 makes it possible to determine the composition of the gas circulating in the main 10 and secondary 20 lines, downstream of the vessels B, C, that is to say it makes it possible to analyze discontinuously the gas taken from the vessels B and C.

As before, this second gas analysis device D2 cooperates with the operating device 4, which itself controls the solenoid valves V5, V6 via electrical connections 37.

The electrical supply of the plant 100 is carried out conventionally by current from the mains, for example at a voltage of between 1 and 600 V, typically 24 V, 230 V or 400 V.

If need be, measurement means (not shown) may be provided in order to determine the pressure of the medical air contained in the vessels A, B, C for storage and homogenization of the gas and optionally retroact via the operating device 4 on the compression unit 31 and/or the production unit 50 so as to regulate the production of the gas, such as air, by taking into account the pressure (or pressures) thus measured. For example, the operating means 4 may be programmed in order to cause shutdown of the flow source 31 and/or triggering of an audio and/or visual alarm, when a pressure sensor arranged at the buffer vessel A detects a pressure or a pressure difference greater than or, conversely, less than a preset threshold value. This type of pressure regulation is well known and will not be described in detail here.

Furthermore, in order to ensure even more effective purification of the air taken in by the compressor 31, one (or more) mechanical filtration devices (not represented in detail) may be provided, arranged at one or more sites between the air source 31 and the hospital network 30. For example, the compression unit may comprise one or more filters at the inlet 32 and/or outlet 33 in order to retain the dust contained in the ambient air and the condensates due to the compression, for example cyclone filters or separators, micron filters or the like.

In general, the plant 100 of the invention for production of medical air on-site, that is to say in a hospital building or the like, therefore employs a three-way solenoid valve adapted to discharge product gas contaminated by impurities to the atmosphere via a purge line connected to one of the ports of the solenoid valve VA, in response to detection of the said contamination by an analysis device D1 cooperating with an operating device 4.

The medical air production plant 100 of the invention may be used directly on the site where the gas is used, that is to say directly in a hospital building or the like. It may therefore be installed directly in a room of the hospital building or outside the said building or in containers, and connected to the network 30 of pipes conveying the gas inside the building.

As already mentioned, and illustrated in FIG. 2, the delivery of the gas stored in the vessels B and C to the consumer site or sites 30 is controlled by an operating method employing alternate provision of the gas, comprising the steps of:

supplying the consumer site 30 with purified gas, that is to say in this case medical air, having a desired composition, that is to say compliant with the European Pharmacopoeia, coming from the third vessel C, simultaneously or substantially simultaneously supplying the second vessel B with gas coming from the first vessel A until the second vessel B is filled, then stopping the supply to the second vessel B, analyzing the composition of the gas stored in the second vessel B, in particular by means of the second gas analysis device D2, in order to determine whether the composition of the gas stored in the second vessel B is compliant with the desired composition, in particular whether it contains a proportion of undesirable impurities such as water vapor, or oil vapors, SOx, COx and NOx, greater than a given maximum value or threshold value, for example the maximum tolerated values set by the Pharmacopoeia or lower values, and as a function of the result of the analysis, sending the gas stored in the second vessel B either to the atmosphere when the analyzed composition is not compliant with the desired composition, or to the consumer site 30 when the analyzed composition is compliant with the desired composition, so as to supply the said consumer site 30 with gas stored in the second vessel B, after stopping the supply of the said consumer site 30 with gas taken from the third vessel C.

When the composition analyzed is not compliant with the desired composition, the second vessel B is emptied and purged fully or substantially fully and the sequence of steps described above is then repeated.

In other words, the second B and third C vessels are alternately subjected to the steps above, which makes it possible to monitor precisely the quality of the gas which they contain and thus prevent noncompliant gas from being sent to the consumer site 30, such as a network of pipes in a hospital building or the like.

In order to implement the steps above, the operating device 4 acts on the valves VA, V1-V8 which are arranged on the main gas line 10, the secondary line 20, on the first purge line 13 and the second purge line 14, as well as on the measurement line 36, 36a, 36b.

Preferably, the gas produced is medical air or medical oxygen, preferably medical air.

These steps are further detailed in FIG. 2, which shows the cycle of filling, analysis and approval of the air produced according to the invention, which is carried out via the vessels B and C, the solenoid valves V1 to V8 controlled by the automaton 4, and the analysis cabinet D2, which itself cooperates with the automaton 4.

More precisely, in FIG. 2 it can be seen that:

after start-up 200 of the cycle according to the invention, the starting situation is as follows: the gaseous content of the vessel C is analyzed and approved 201 for provisioning the network 30 of the hospital with medical gas, such as air. The valve V4 is then open and the vessel B is empty. The valves V1 to V3 and V5 to V8 are closed.

the vessel B is then filled, by opening 202 the valve V1, with purified air coming from the first vessel A (cf. FIG. 1) until the vessel B is fully filled.

when the vessel B is full 203, that is to say after a given filling time, the valve V1 is closed and the valve V5 is opened (at 204).

then (at 205), the content of the vessel B is analyzed. At the end of the analysis, the valve V5 is closed.

if the analysis results at 207 are compliant ("yes") with the specifications desired for the gas produced, the content of the vessel B is approved but remains on standby until the vessel C is fully empty (211).

conversely, if the analysis results are not compliant ("no") with the specifications, the valve V7 is opened 208 and the content of the vessel B is discharged 209 to the atmosphere, via the vent line 11 of FIG. 1, as already explained. When the vessel B is empty, the valve V7 is closed 210 and the filling cycle restarts at 202 as before, until a compliant analysis result is obtained (at 207).

At 211, when the vessel C is empty, the valve V4 is closed and the valve V2 is opened (at 212). The vessel B then in turn supplies 213 the hospital network 30 with medical air.

In parallel, the vessel C is filled (at 214) with medical gas by opening the valve V3, until a full vessel C is obtained (at 215).

Then, in a similar way to that which was carried out on the vessel B, the content of the vessel C is analyzed 217 and the automaton 4 causes closure of the valve V3 and opening of the valve V6 (at 216).

At the end of the analysis, the automaton 4 causes closure 218 of the valve V6.

Again, if the analysis results are compliant ("yes") with the specifications (at 219), the content of the vessel C is approved and remains on standby until the vessel B is empty (at 223).

Conversely, if the analysis results are not compliant ("no") with the specifications, the valve V8 is opened 220 and the content of the vessel C is discharged to the outside, via the vent 12 and the purge line 11 of FIG. 1. When the vessel C is empty, the valve V8 is closed 222 and the filling cycle restarts at 214.

When the vessel B is empty, the automaton 4 causes closure of the valve V2 and opening of the valve V4. The vessel B then in turn supplies (224) the hospital network 30 with medical air.

Finally, the cycle restarts from the beginning 225.

This cycle is particularly effective because it prevents the consumer site or sites 30 from running dry, even when contamination of the gas is detected, that is to say an impurity level greater than the desired specifications, by virtue of provision of air or medical gas to the said consumer site 30 alternately, that is to say coming either from the vessel B or from the vessel C.

This makes it possible not only to avoid contaminating the consumer site 30 with noncompliant gas, but also to minimize the use of air coming from a backup source 3 (cf. FIG. 1).

It will be understood that many additional changes in the details, materials, steps and arrangement of parts, which have been herein described in order to explain the nature of the invention, may be made by those skilled in the art within the principle and scope of the invention as expressed in the appended claims. Thus, the present invention is not intended to be limited to the specific embodiments in the examples given above.

What is claimed is:

1. An on-site medical gas production plant (100), comprising:
    a gas purification unit (50) adapted to produce a purified gas from a supply gas,
    a main gas line (10) supplied with a gas by the gas purification unit (10) and comprising, in series, a first vessel (A) for storing a purified gas and a second vessel (B) for storing the purified gas, and
    a secondary line (20) fluidically connected to the main line (10), downstream of the first vessel (A) for storing the purified gas and comprising a third vessel (C) for storing the purified gas,
    a downstream gas analysis device (D2) arranged so as to determine the level of at least one given impurity in the purified gas, downstream of both the second vessel (B) and the third vessel (C),
    a first solenoid valve (V1), arranged on the main gas line (10) between the first vessel (A) for storing the purified gas and the second vessel (B) for storing the purified gas,
    a second solenoid valve (V3), arranged on the secondary gas line (20) between the first vessel (A) and the third vessel (C) for storing the purified gas,
    a third solenoid valve (V2), arranged on the main gas line (10) downstream of the second vessel (B) for storing the purified gas,
    a fourth solenoid valve (V4), arranged on the secondary gas line (20) downstream of the third vessel (C) for storing the purified gas, and
    an operating device (4) which controls the opening or closing of the said solenoid valves (V1 to V4) in response to at least one impurity level measurement signal received from the downstream gas analysis device (D2).

2. The plant according to claim 1, wherein a three-way solenoid valve (VA) is arranged on the main gas line (10) between the gas purification unit (50) and the first storage vessel (A), the three-way solenoid valve being connected to the atmosphere (at 12) via a vent line (11), and being controlled by the operating device (4).

3. The plant according to claim 1, wherein the plant includes an initial gas analysis device (D1) having a first measurement line (29) fluidically connected (at 28) to the main line (10), upstream of the first storage vessel (A).

4. The plant according to claim 3, wherein the downstream gas analysis device (D2) has at least one second measurement line (36; 36a; 36b) fluidically connected (at 34, 35) directly or indirectly to the main line (10) and/or to the secondary line (20), downstream of the second storage vessel (B) and/or downstream of the third storage vessel (C), respectively.

5. A method for operating an on-site medical gas production plant (100) comprising a main gas line (10) comprising, in series, a first vessel (A) for storing a purified gas and a second vessel (B) for storing the purified gas, and a secondary line (20) fluidically connected to the main line (10), downstream of the first vessel (A) for storing the purified gas, and comprising a third vessel (C) for storing the purified gas, the main gas line (10) and the secondary line (20) each supplying at least one gas consumer site (30), comprising the steps of:
   a) supplying the said at least one consumer site (30) with the purified gas having a desired composition coming from the third vessel (C),
   b) supplying the second vessel (B) with the purified gas coming from the first vessel (A) for storing the purified gas,
   c) stopping the supply of the second vessel (B) with the purified gas coming from the first vessel (A) when the second vessel (B) is filled with the purified gas,
   d) analyzing the composition of the purified gas stored in the second vessel (B) to determine whether the composition of the purified gas stored in the second vessel (B) is compliant with a desired composition,
   e) as a function of the result of step d), sending the purified gas stored in the second vessel (B):
      i) either to the atmosphere when the analyzed composition is not compliant with the desired composition,
      ii) or to the said at least one consumer site (30) when the analyzed composition is compliant with the desired composition.

6. The method according to claim 5, wherein in step e) ii), the at least one consumer site (30) starts to be supplied with the purified gas stored in the second vessel (B) after a shutdown of a supply of the said consumer site (30) with a purified gas taken from the third vessel (C).

7. The method according to claim 5, wherein steps a) and b) are at least in part simultaneous.

8. The method according to claim 5, wherein in step e) i), the second vessel (B) is emptied fully or substantially fully and steps b) to e) are repeated.

9. The method according to claim 5, wherein the second (B) and third (C) vessels are operated so as to undergo steps a) to e) alternately.

10. The method according to claim 5, wherein the gas supplying the second (B) and third (C) vessels is produced by a gas purification unit (50) comprising at least a first adsorber (1, 2) containing at least one bed of at least one adsorbent material, the said at least one adsorber (1, 2) being supplied by a gas compression unit (31) with a gas to be purified.

11. The method according to claim 10, further comprising a second adsorber (1, 2) operated alternately with the first absorber.

12. The method according to claim 5, wherein in step d), the composition of the gas is analyzed by a downstream gas analysis device (D2) configured to determine the level of at least one impurity in the gas, downstream of the second (B) and third (C) vessels.

13. The method according to claim 12, wherein the impurity or impurities are selected from NOx, SOx, COx, water vapor, and oil vapors or other hydrocarbon vapors.

14. The method according to claim 5, wherein steps a) to e) are controlled by an operating device (4) acting on valves (VA, V1-V8) arranged on the main gas line (10), the secondary line (20), on a first purge line (13) fluidically connected to the main line (10) downstream (24) of the second vessel (B), and/or a second purge line (14) fluidically connected to the secondary line (20) downstream (26) of the third vessel (C) and/or a measurement line (36, 36a, 36b; at 34, 35).

15. The method according to claim 5, wherein the gas produced is medical air or medical oxygen.

16. The method according to claim 14, wherein the gas produced is medical air containing (by volume) from 20.4% to 21.4% oxygen, at most 500 ppm $CO_2$, at most 5 ppm CO, at most 1 ppm $SO_2$, at most 2 ppm NO and $NO_2$, at most 67 ppm water, at most 0.1 mg/m$^3$ oil, and nitrogen.

* * * * *